United States Patent [19]
Chen et al.

[11] Patent Number: 5,876,427
[45] Date of Patent: Mar. 2, 1999

[54] COMPACT FLEXIBLE CIRCUIT CONFIGURATION

[75] Inventors: James C. Chen, Bellevue, Wash.; Brent Wiscombe, Mesa, Ariz.

[73] Assignee: Light Sciences Limited Partnership, Issaquah, Wash.

[21] Appl. No.: 787,775

[22] Filed: Jan. 29, 1997

[51] Int. Cl.$^6$ .................................................. A61N 21/00
[52] U.S. Cl. .............................. 607/88; 607/89; 607/116; 607/152; 604/20
[58] Field of Search .................................... 600/373–381, 600/393–394; 607/88, 115–116, 152, 154; 604/19–21; 606/41

[56] References Cited

U.S. PATENT DOCUMENTS

| | | | |
|---|---|---|---|
| 4,634,631 | 1/1987 | Gazit et al. | 428/421 |
| 4,647,508 | 3/1987 | Gazit et al. | 428/421 |
| 5,215,087 | 6/1993 | Anderson et al. | 600/392 |
| 5,246,003 | 9/1993 | DeLonzer | 600/344 |
| 5,314,463 | 5/1994 | Camps et al. | 607/129 |
| 5,324,322 | 6/1994 | Grill et al. | 607/118 |
| 5,445,608 | 8/1995 | Chen et al. | 604/20 |
| 5,499,981 | 3/1996 | Kordis | 607/116 X |
| 5,505,730 | 4/1996 | Edwards | 606/41 |
| 5,524,328 | 6/1996 | Martyniuk et al. | 600/378 X |
| 5,554,178 | 9/1996 | Dahl et al. | 607/122 |
| 5,678,544 | 10/1997 | DeLonzor | 600/344 |

FOREIGN PATENT DOCUMENTS

WO93/21842  11/1993  WIPO .............................. A61B 17/36

OTHER PUBLICATIONS

Barth et al., "Monolithic Silicon Fabrication Technology for Flexible Circuit and Sensor Arrays," pp. 83–86.

Schmidt et al., "Light–emitting Diodes as a Light Source for Intraoperatiave Photodynamic Therapy," *Neurosurgery*, vol. 38, No. 3, Mar. 1996, pp. 552–557.

Gomez, "Ultrasonic Ventriculostomy Stylet," *Neurosurgery*, vol. 37, No. 5, Nov. 1995, pp. 1020–1021.

*Primary Examiner*—Jeffrey R. Jastrzab
*Assistant Examiner*—Ryan Carter
*Attorney, Agent, or Firm*—Ronald M. Anderson

[57] ABSTRACT

A flexible probe constructed using a flexible circuit having a small cross-sectional profile. In the various disclosed embodiments of the flexible circuit, a flexible substrate includes a plurality of conductive traces that extend along opposite surfaces of the substrate. Light emitting devices (or other electronic devices) are mounted at spaced-apart intervals along the length of the conductive traces using a conductive adhesive/solder. A conductor couples a terminal on the outwardly facing side of each of the light emitting devices to the conductive trace that is disposed on the opposite side of the substrate. In one embodiment, this conductor comprises a short conductive bar that extends between the terminals of pairs of the light emitting devices that are mounted on opposite sides of the flexible substrate so that the pair of light emitting devices are connected in series. In another embodiment, the flexible substrate includes an outwardly extending arm of the conductive trace that wraps around the edge of the flexible substrate to connect to the light emitting device mounted on the opposite side thereof. In each embodiment, a substantially smaller cross-sectional profile is achieved compared to a previous approach in which the conductive traces providing power to a light emitting device were located on the same side of the flexible substrate and fly wires were used to connect the light emitting devices to the conductive traces.

28 Claims, 3 Drawing Sheets

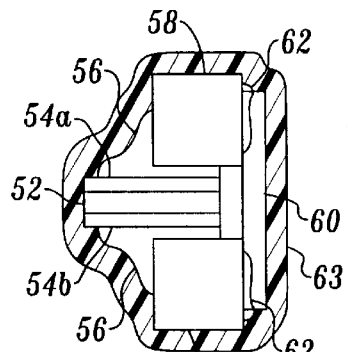
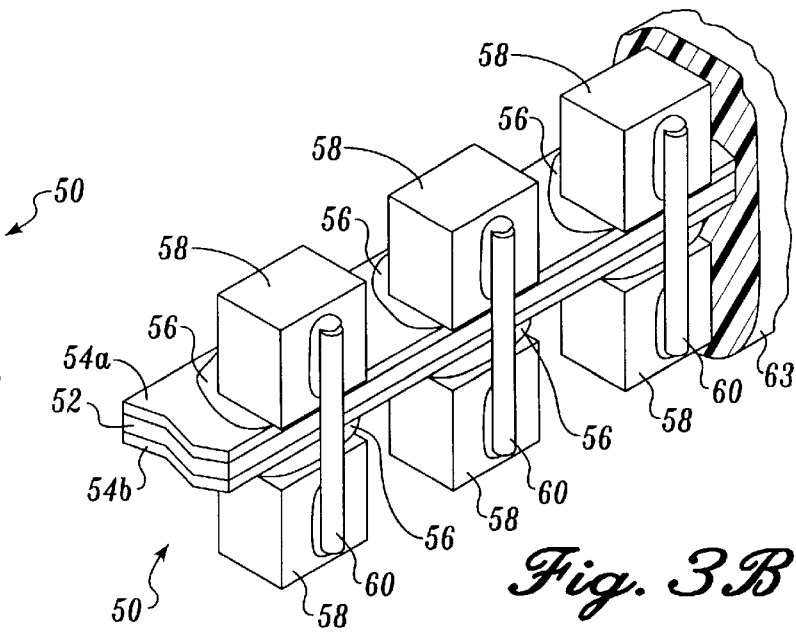
*Fig. 3A*  *Fig. 3B*
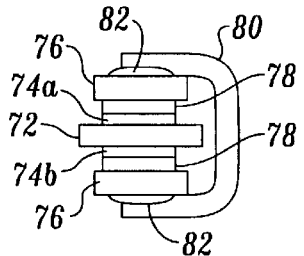
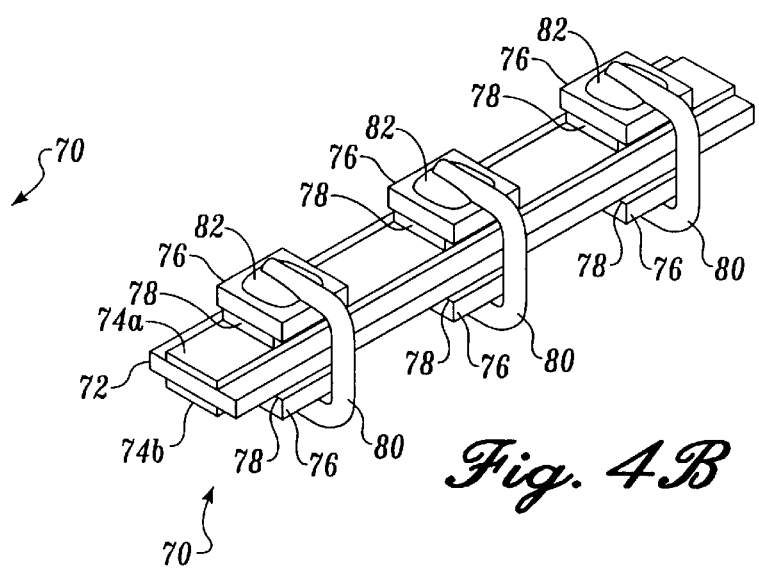
*Fig. 4A*  *Fig. 4B*
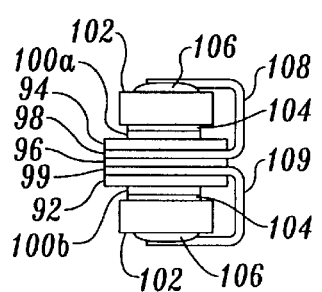
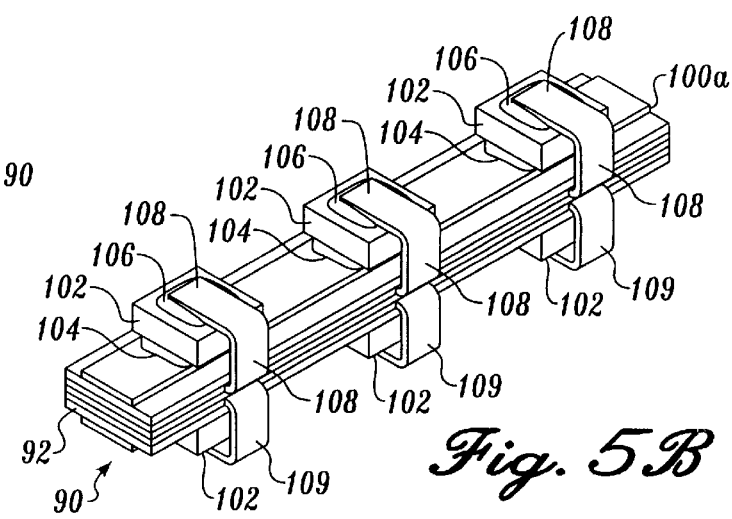
*Fig. 5A*  *Fig. 5B*

5,876,427

COMPACT FLEXIBLE CIRCUIT CONFIGURATION

FIELD OF THE INVENTION

The present invention is generally directed to a circuit substrate having conductive traces on which are mounted a plurality of electrical devices used for administering a medical treatment, and more specifically, is directed to a probe that is inserted within a patient's body to administer the medical treatment and which includes a flexible circuit substrate on which are disposed conductive traces that convey electrical signals to the plurality of electrical devices.

BACKGROUND OF THE INVENTION

Several embodiments of light emitting probes designed to be transcutaneously introduced into the body of a patient and positioned at a desired treatment site to administer photodynamic therapy (PDT) using a plurality of light sources are taught in commonly assigned U.S. Pat. No. 5,445,608, the drawings and disclosure of which are specifically incorporated herein by reference. Several different embodiments of such probes are illustrated and discussed il this prior patent. Each of the probes disclosed in this reference includes a plurality of light sources that are mounted on a relatively stiff or inflexible substrate and enclosed within a transparent envelope through which light emitted by the light sources is transmitted to irradiate a tumor or other cells that are to be destroyed by PDT. The light sources used on the probes taught by this reference are preferably light emitting diodes (LEDs); however, almost any light source capable of emitting light in a waveband corresponding to an absorption waveband of a photoreactive agent that has been applied to the tumor or other tissue to be destroyed can be used. By inserting one of these probes into a patient's body, moving the probe to an internal treatment site, and using the probe for applying PDT, abnormal cells or other organisms at the treatment site can be destroyed without significant adverse impact on adjacent normal tissue.

None of the implantable light emitting probes disclosed in the above-referenced patent include light sources mounted on flexible substrates. There are many applications for PDT in which it would be advantageous to use a flexible substrate for mounting the LEDs or other light sources on a probe employed to administer the PDT, e.g., so that the probe can be threaded into a treatment site through a curved passage within the patient's body without risk of perforation of the wall of the passage. In contrast to the relatively inflexible substrate used in the probes disclosed in the above-referenced patent, a flexible PDT probe having a small cross-sectional size, e.g., less than 2 mm, can be more readily maneuvered through body passages using conventional endoscopic techniques, enabling the flexible probe to be inserted to provide a medical therapy, such as the administration of PDT, to a treatment site. In addition, a small cross-sectional area flexible probe is less likely to cause bleeding upon insertion interstitially at a treatment site and become infected after insertion. The prior art does not disclose a flexible probe capable of providing these capabilities.

To address the need for such devices, commonly assigned U.S. patent applications, Ser. No. 08/613,390 filed Mar. 7, 1996, now U.S. Pat. No. 5,800,478, and a continuation-in-part thereof, Ser. No. 08/633,171 filed Apr. 16, 1996, now U.S. Pat. No. 5,766,234, both entitled "Flexible Microcircuits for Internal Light Therapy," disclose several different embodiments of flexible probes. These embodiments include a relatively small diameter, elongate flexible probe. The elongate probe comprises a flexible substrate on which are mounted a plurality of light emitting devices, in a spaced-apart array. The light emitting devices are mounted on each side of the substrate, and are electrically connected to two flexible conductive traces that extend along the surface of each side. The light sources each include terminals disposed on opposite sides of the device. One terminal is electrically connected using solder or a conductive adhesive to one of the two traces. A fly wire (very small gage) couples the other terminal to the other conductive trace. While this arrangement provides a workable flexible probe that is able to bend without damage as the probe is inserted through a small diameter passage, the probe has a larger diameter than desired because the width of the flexible substrate required for this configuration is slightly greater than the sum of the width of the light emitting devices and the width of the two conductive traces. The resulting configuration is also subject to damage when handled before final fabrication of the probe is completed, because the fragile fly wires are exposed until the substrate and mounted light sources are encapsulated in a flexible, optically transparent, biocompatible material. Thus, a more compact arrangement that is more robust and capable of automated fabrication is desirable. Ideally, it should be possible to fabricate a flexible elongate probe having a cross-sectional diameter of less than 0.15 cm, i.e., the width of the substrate should be only slightly greater than the width of the light sources mounted thereon.

It will also be apparent that a flexible probe having a smaller diameter so that it can more readily be introduced to a treatment site has utility for implementing medical therapies other than PDT. For example, a small diameter flexible probe that includes an ultrasonic transmitter and/or ultrasonic receiver can readily be inserted into an organ or through a lumen to carry out an ultrasound scan of surrounding tissue. Furthermore, a small diameter flexible probe that is used to administer PDT can be provided with electronic components capable of carrying out additional functions. For example, a sensor to determine the efficacy of the PDT treatment might be included on the flexible probe, in addition to the plurality of light sources that are used to provide light to a treatment site.

A relatively smaller diameter flexible probe on which one or more electrical circuits for administering a medical treatment or a sensing device is mounted can more readily be threaded into an internal site within a patient's body than a larger diameter probe, and the insertion procedure can be implemented with less trauma to the patient. In addition, a configuration that eliminates use of the fly wires to couple the terminal of a device to a conductive trace should improve the durability of the probe. Producing a smaller diameter probe that is more robust than that of previous designs is clearly a desirable objective.

SUMMARY OF THE INVENTION

In accordance with the present invention, a flexible circuit for use in a probe intended to be inserted into a patient's body is defined that includes an elongate flexible substrate comprising a material having good dielectric properties. The flexible substrate has two opposed surfaces, including a first surface and a second surface. A first conductive trace extends along the first surface of the flexible substrate, and similarly, a second conductive trace extends along the second, opposite surface of the flexible substrate. A plurality of first electrical devices are mounted in spaced-apart array along the first surface of the flexible substrate. Each of these electrical devices has a first electrical terminal that is electrically connected to the first conductive trace and a second electrical terminal that is spaced apart from the first electrical terminal. Link means are provided for electrically coupling the second electrical terminals of the plurality of first electrical devices to the second conductive trace that is on the second surface of the flexible substrate. The first and second conductive traces and the link means carry an electrical current that energizes the plurality of first electrical devices. A biocompatible, flexible material encapsulates the flexible substrate, the first and second conductive traces, the link means, and the plurality of first electrical devices.

The flexible circuit can further comprise a plurality of second electrical devices that are mounted in spaced-apart array along the second surface. Each of said plurality of second electrical devices has a first electrical terminal. A second electrical terminal is spaced apart from the first electrical terminal and is in electrical contact with the second electrically conductive trace. In one preferred embodiment, the link means electrically connect the second electrical terminals of the plurality of first electrical devices to the first electrical terminals on the plurality of second electrical devices, so that the electrical current carried by the first and second electrical traces and the link means flows through the plurality of first electrical devices, in series with the plurality of second electrical devices. This electrical current thus also energizes the plurality of second electrical devices. In this embodiment, the link means preferably comprise relatively straight segments of wire.

In another preferred embodiment, the link means comprise first conductors that extend between and are connected to the second electrical terminals of the plurality of first electrical devices and to the second conductive trace; the link means also include second conductors that extend between and are connected to the first electrical terminals of the plurality of second electrical devices and to the first conductive trace. In this embodiment, the electrical current carried by the first and second electrical traces and the link means flows through the plurality of first electrical devices in parallel with the plurality of second electrical devices and thus also energizes the plurality of second electrical devices. The second terminals of the plurality of first electrical devices and the first terminals of the plurality of second electrical devices each face toward an edge of the flexible substrate. The link means preferably comprise conductors that extend past the edge of the flexible substrate to connect the second terminals of the plurality of first electrical devices with the first terminals of the plurality of second electrical devices.

In yet another embodiment, the second conductive trace comprises a conductive foil having a plurality of side arms extending transversely off the edge of the second surface of the flexible substrate. In this embodiment, the plurality of side arms (i.e., the link means) are bent to connect to the second electrical terminals of the plurality of first electrical devices. In one form of the invention, second surfaces of two flexible circuits are bonded together forming an assembly having first electrical devices mounted on opposite sides thereof.

In still another embodiment, the first and second conductive traces each comprise a conductive foil; the conductive foil of the first conductive trace has a plurality of first side arms extending transversely off an edge of the first surface of the flexible substrate, and similarly, the conductive foil of the second conductive trace has a plurality of second side arms extending transversely off an edge of the second surface. For this embodiment, the link means comprise the plurality of first side arms, which are bent to connect to the first electrical terminals of the plurality of second electrical devices, and the plurality of second side arms, which are bent to connect to the second electrical terminals of the plurality of first electrical devices.

While not limited to such devices, the plurality of first and second electrical devices preferably comprise light emitting devices for providing a light therapy at a treatment site within the patient's body. In each of the preferred embodiments, the plurality of first and second electrical devices are mounted on the first and second surfaces of the flexible substrate using an adhesive that is electrically conductive. The adhesive electrically couples the first electrical terminals of the plurality of first electrical devices to the first conductive trace, and the second electrical terminals of the plurality of second electrical devices to the second conductive trace.

Another aspect of the present invention is directed to a method for producing a flexible probe having a compact cross-sectional dimension, for use in rendering a medical treatment to a treatment site within a patient's body. The method includes steps that are generally consistent with the functions implemented by the elements of the flexible circuit discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 3A is an end view of a first embodiment of the present invention that is used to produce a flexible probe having a substantially smaller cross section than the configurations shown in FIGS. 1A, 1B, and 2;

FIG. 3B is an isometric view of a portion of the embodiment of FIG. 3A;

FIG. 4A is an end view of a second embodiment of the flexible circuit in accord with the present invention;

FIG. 4B is an isometric view of the embodiment of FIG. 4A;

FIG. 5A is an end view of a third embodiment of the present invention, in which two substrates are joined together, back-to-back;

FIG. 5B is an isometric view of a portion of the third embodiment shown in FIG. 5A;

DESCRIPTION OF THE PREFERRED EMBODIMENT

As noted above in the Background of the Invention, earlier versions of a flexible probe have been developed for providing light therapy to a treatment site within a patient's body. Due to their elastic properties, the flexible probes can more readily be inserted to a specific treatment site using endoscopic techniques. In addition to light therapy, it is also contemplated that other medical devices mounted on flexible probes can be advanced to a treatment site in much the same manner.

Figure 1A:
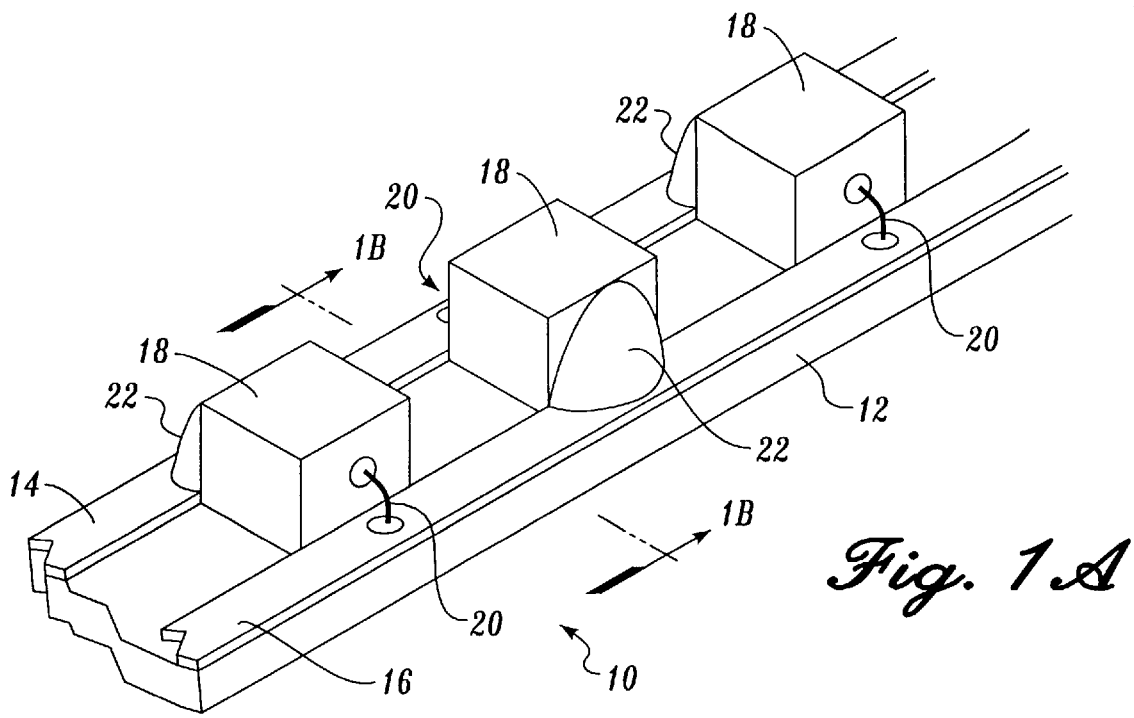
FIG. 1A is an isometric view of a portion of a flexible substrate showing a plurality of light sources mounted on one surface in accord with an earlier configuration in which the diameter of a probe was relatively wider than in the present invention.
Figure 1B:
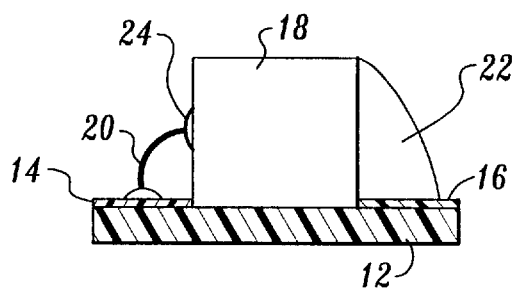
FIG. 1B is an end view of the configuration for a flexible substrate shown in FIG. 1A.

An example of a previous embodiment of a flexible circuit 10 is illustrated in FIGS. 1A and 1B. The flexible circuit is supported by a flexible substrate 12 comprising a polymeric plastic material, which is selected for its elastomeric properties that enable it to readily bend without breaking. On the upper surface of flexible substrate 12 (as shown in FIGS. 1A and 1B) are spaced-apart conductive traces 14 and 16. These conductive traces are disposed on each side of light emitting devices 18 and are thus spaced apart by approximately the width of the light emitting devices. Light emitting devices 18 are adhesively attached to flexible substrate 12 at spaced-apart intervals along the longitudinal length of the flexible substrate. Conductive traces 14 and 16 are connected to a source of electrical current (not shown) that is remote and separate from the flexible circuit. In this previous design, light emitting devices 18 comprise light emitting diodes (LEDs) and thus can be selectively energized, depending upon the polarity of the DC voltage applied to the devices. To enable specific light emitting devices to be energized depending upon the polarity of the voltage applied to conductive traces 14 and 16, the light emitting devices are mounted on flexible substrate 12, with their terminals arranged in a specific polarity. Fly wires 20 extend from the terminals on one side of a light emitting device to one of the conductive traces, while on the opposite side of that light emitting device, a conductive adhesive or solder droplet 22 provides electrical continuity between the terminal and the conductive trace.

A tubular probe incorporating flexible circuit 10 would have a diameter slightly greater than the width of flexible substrate 12. Because of the configuration of the flexible circuit, the width of flexible substrate 12 is slightly greater than or equal to the sum of the widths of conductive traces 14 and 16 and the width of the light emitting devices. In addition, the fly wires 20 extending between the conductive traces and the terminals on the sides of the light emitting devices are the components most likely to fail in this configuration. The present invention addresses these two problems.

Figure 2:
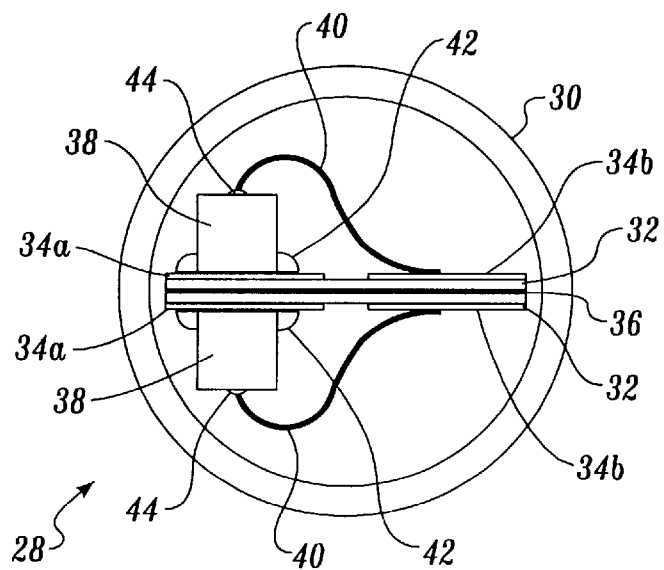
FIG. 2 is an end view of another configuration for mounting light sources on both sides of a flexible substrate, as previously developed.

An alternative embodiment of the previous design of a flexible probe 28 is illustrated in FIG. 2. Since this is a cross-sectional view, only limited details concerning the multiplicity of light emitting devices 38 that are attached to one side of flexible substrates 32 are illustrated. In this embodiment, two flexible substrates 32 are attached back-to-back by an adhesive layer 36. On the outwardly or oppositely facing surfaces of flexible substrates 32 are mounted light emitting devices 38, spaced-apart along the length of the flexible substrates. Also extending longitudinally along the length of these flexible substrates 32 are conductive traces 34a and 34b. On the outwardly facing surface of each substrate 32, conductive trace 34a extends generally parallel and spaced apart from conductive trace 34b. Conductive traces 34a and 34b on each of the oppositely facing surfaces of the flexible substrate are connected to a power source that provides an electrical current for energizing light emitting devices 38. While not shown, it should be understood that the power source may be disposed either internally within the patient's body, or may be energized from an external source by an electromagnetic coupling technique, RF coupling, or other appropriate means.

Light emitting devices 38 are adhesively attached to conductive traces 34a using a conductive adhesive or solder 42. A terminal 44 on each light emitting device is coupled through a fly wire 40 to one of the conductive traces 34b. Fly wires 40 are bonded to conductive traces 34b. Surrounding the conductive traces, light emitting devices, and flexible substrates is a cylindrical optically transparent and biocompatible envelope 30. Envelope 30 protects the flexible circuit from damage, and is hermetically sealed around the flexible substrates. Preferably, envelope 30 comprises a plastic polymer selected for its flexibility and optical transparency.

Again, it will be evident that the diameter of flexible probe 28 is determined primarily by the width of flexible substrate 32, since the flexible substrate must fit within envelope 30. Clearly, it would be desirable to eliminate fly wires 40 from the assembly illustrated in FIG. 2 and to reduce the width of the flexible substrates required to produce a flexible circuit so that the diameter of envelope 30, and thus, the diameter of the flexible probe can also be reduced.

Turning now to FIGS. 3A and 3B, a first flexible circuit 50 having a substantially smaller cross-sectional profile is illustrated. Flexible circuit 50 includes a flexible substrate 52 having conductive traces 54a and 54b extending longitudinally along opposite surfaces. At spaced-apart intervals along the longitudinal axis of flexible substrate 52 are disposed light emitting devices 58. The light emitting devices are mounted to conductive traces 54a and 54b using a conductive adhesive/solder 56 and are disposed so that a light emitting device mounted on conductive trace 54a is disposed opposite a light emitting device mounted on conductive trace 54b. Conductive traces 54a and 54b are coupled to a source of an electrical current (not shown). Accordingly, light emitting devices 58 that are mounted to conductive trace 54a are electrically connected to it through conductive adhesive/solder 56, while those mounted on conductive trace 54b are electrically connected to that conductive trace in a similar fashion. A conductive bar 60 extends adjacent the edge of flexible substrate 52 and is mechanically and electrically connected to the terminals of light emitting devices 58 that are mounted on opposite sides of flexible substrate 52 by a conductive adhesive/solder 62. The light emitting devices are thus joined in series by the conductive bar.

It will be apparent that the height and width of flexible circuit 50 is substantially less than that of the earlier designs illustrated in FIGS. 1A, 1B, and 2. An optically transparent flexible material 63 that is biocompatible and serves the same purpose as envelope 30, which is shown in FIG. 2, encapsulates flexible circuit 50 and each of the other embodiments of the flexible circuits discussed below. However, the encapsulating material is omitted from the drawings depicting each of other embodiments of the flexible circuits in order to simplify the illustrations.

A second embodiment of the present invention is illustrated in FIGS. 4A and 4B, which show a flexible circuit 70. Flexible circuit 70 includes an elongate flexible substrate 72 that extends longitudinally. Conductive traces 74a and 74b extend longitudinally along the opposite surfaces of flexible substrate 72. On opposite sides of flexible substrate 72 are mounted light emitting devices 76. These light emitting devices are connected to conductive traces 74a and 74b using a conductive adhesive/solder 78, which is in electrical contact with the terminals on one side of the light emitting devices. On an opposite side of each light emitting device is another terminal that is connected to a U-shaped conductor 80 that extends from one side of the flexible substrate around to the opposite side and which is sized so that the ends of the U-shaped conductor are seated on the outwardly facing surfaces of light emitting devices 76, overlying the terminals of the devices. A conductive adhesive/solder 82 adheres and provides electrical conduction between these terminals and the ends of U-shaped conductors 80. Thus, flexible circuit 70 is similar to flexible circuit 50 in that pairs of the light emitting devices mounted on opposite sides of the flexible substrate are connected in series, but in the present embodiment, the U-shaped conductor performs the same function as conductive bar 60 in the preceding embodiment. Tile desired low profile and minimal width of flexible circuit 70 is thus achieved, enabling the flexible circuit to be used in a flexible probe having a relatively small cross-sectional diameter.

A somewhat different approach is used for constructing a flexible circuit 90, as illustrated in FIGS. 5A and 5B. For this flexible circuit, two flexible substrates 92 and 94 are coupled back-to-back. A plurality of light emitting devices 102 are mounted on flexible substrate 94 at spaced-apart intervals. Light emitting devices 102 have terminals disposed on opposite facing sides of the devices. The terminal on the lower surface of each device is connected to a conductive trace 100a that extends along the length of flexible substrate 94 and at one end is connected to a power source (not shown). A conductive adhesive/solder layer 104 both mechanically and electrically connects each light emitting device 102 to conductive trace 100a.

Similarly, light emitting devices 102 are mounted in spaced-apart array on conductive trace 100b, which extends along the length of flexible substrate 92. Light emitting devices 102 are also connected to conductive trace 100b using conductive adhesive/solder layer 104. The lower surface of flexible substrate 94 (as shown in the Figures.) includes a longitudinally extending conductive trace 98. At spaced-apart intervals corresponding to the spacing between light emitting devices 102, conductive trace 98 includes outwardly extending arms 108 that are not adhered to the flexible substrate, but instead are formed into a U-shape to connect to the upper terminals of the light emitting devices mounted on flexible substrate 94. Again, conductive adhesive/solder 106 electrically and mechanically is employed to couple the free ends of outwardly extending arms 108 to the terminal on the top of the light emitting devices.

Similarly, a conductive trace 99 extends along the inwardly facing side of flexible substrate 92 and at spaced-apart intervals corresponding to the spacing between the light emitting devices mounted on flexible substrate 92 includes foil arms 109 that are formed into a U-shape so that the ends of the arms are attached to the terminals on the bottom of the light emitting devices mounted on flexible substrate 92. An adhesive layer 96 joins flexible substrates 92 and 94 together back-to-back. Adhesive layer 96 may be conductive if it is desired that conductive traces 98 and 99 are at a common polarity. Alternatively, the conductive traces can be electrically insulated from each other so that the LEDs mounted on the outer surface of flexible substrate 94 are separately energized from those mounted on the outer surface of flexible substrate 92. The resulting configuration provides two separate circuits, but is still relatively compact, having a substantially smaller cross-sectional size than the designs previously developed and illustrated in FIGS. 1A, 1B, and 2.

Figure 6A:
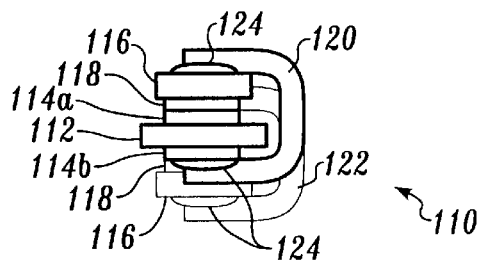
FIG. 6A is an end view of a fourth embodiment of the present invention.
Figure 6B:
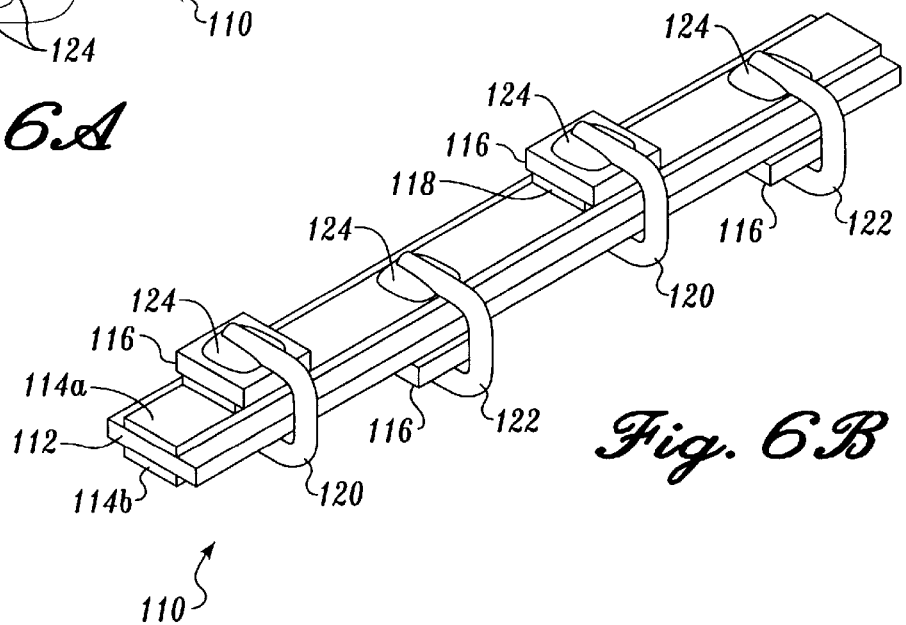
FIG. 6B is an isometric view of a portion of the fourth embodiment shown in FIG. 6A.

Referring to FIGS. 6A and 6B, a flexible circuit 110 is disposed having a further alternative configuration. In this embodiment, an elongate flexible substrate 112 has two outwardly facing surfaces on which are respectively disposed conductive traces 114a and 114b. These conductive traces are connected to a source of electrical current (not shown), generally as noted above in connection with the preceding embodiments. A plurality of light emitting devices 116 are mounted in spaced-apart array along the length of conductive trace 114a. Similarly, light emitting devices 116 are mounted in spaced-apart array along the length of conductive trace 114b. To mount the light emitting devices to the conductive traces, a conductive adhesive/solder 118 is applied between the lower terminal of the light emitting device and the conductive trace. On the opposite sides of the light emitting devices mounted on conductive trace 114a, a U-shaped conductor 120 is attached to the terminal of the light emitting device with a conductive adhesive/solder 124. The other end of conductor 120 extends around the edge of flexible substrate 112 and is attached to conductive trace 114b with conductive adhesive/solder 124. Similarly, a U-shaped conductor 122 is attached to the lower terminal (as shown in FIGS. 6A and 6B) of the light emitting devices mounted on conductive trace 114b. Thus, in this configuration, the light emitting devices mounted on opposite sides of flexible substrate 112 arc not connected in series, but instead, are connected in parallel. The cross-sectional size of flexible circuit 110 again is much smaller than that of the prior designs shown in FIGS. 1A, 1B, and 2.

Figure 7A:
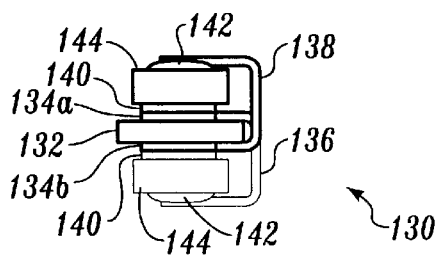
FIG. 7A is an end view of a fifth embodiment of the flexible probe in accord with the present invention.
Figure 7B:
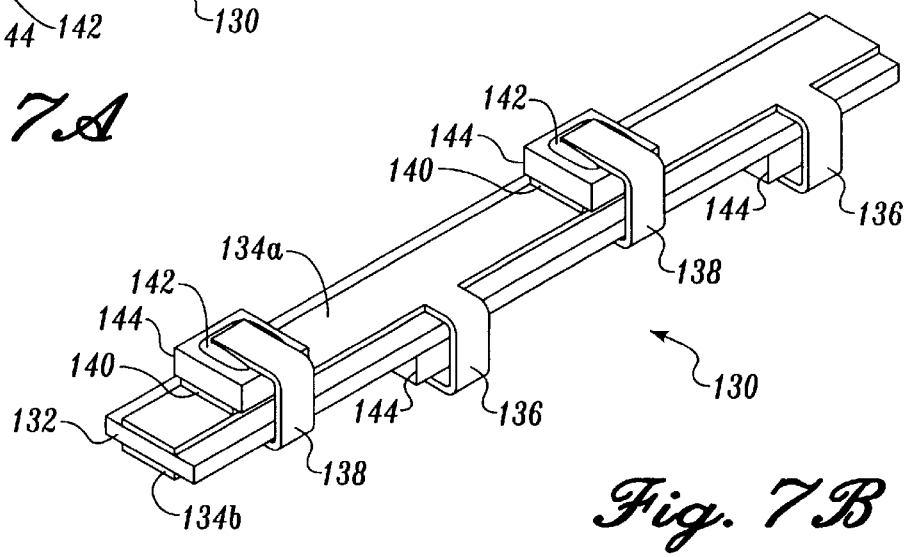
FIG. 7B is an isometric view of the fifth embodiment shown in FIG. 7A.

Finally, an embodiment for a flexible circuit 130 is illustrated in FIGS. 7A and 7B. Flexible circuit 130 is very similar to flexible circuit 110, since it includes an elongate flexible substrate 132 having opposite sides along the length of which extend conductive traces 134a and 134b. Light emitting devices 144 are mounted at spaced-apart intervals along the length of both conductive traces 134a and 134b, using a conductive adhesive/solder layer 140. The light emitting devices mounted to conductive trace 134a are disposed at positions interleaved relative to the position of the light emitting devices mounted on conductive trace 134b.

Instead of using the U-shaped conductors employed in flexible circuit 110, flexible circuit 130 includes conductive traces 134a and 134b with outwardly extending arms 136 and 138, respectively, which are bent around the edge of flexible substrate 132 and are connected to the outwardly facing terminals of light emitting devices 144 using conductive adhesive/solder 142. Outwardly extending arms 136 and 138 are integrally formed from the foil used for the conductive traces. It is contemplated that the process of constructing flexible circuit 110 should be easily automated. Flexible circuit 130 is extremely compact, having a very small cross-sectional profile, which enables a flexible probe incorporating the flexible circuit to be correspondingly small in diameter.

While each of the embodiments of the flexible circuit disclosed above include light emitting devices, it will be apparent that other electronic devices used for providing a medical therapy can be alternatively mounted on the flexible circuits in much the same way as the light emitting devices. The present invention enables various configurations of flexible circuits to be produced that have a relatively small cross-sectional profile. Consequently, a flexible probe made using the present invention and intended for therapeutic and diagnostic purposes can be of small diameter, readily inserted within the body, and advanced to a desired treatment site.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A flexible circuit for use in a probe intended to be inserted into a patient's body, comprising:
    (a) an elongate flexible substrate comprising a dielectric material, said flexible substrate having two opposed surfaces, including a first surface and a second surface;
    (b) a first conductive trace extending along said first surface of the flexible substrate;
    (c) a second conductive trace extending along said second surface of the flexible substrate;
    (d) a plurality of first electrical devices mounted in spaced-apart array along said first surface of the flexible substrate, each of said plurality of first electrical devices having:
        (i) a first electrical terminal that is electrically connected to said first conductive trace; and
        (ii) a second electrical terminal spaced apart from said first electrical terminal;
    (e) link means for electrically coupling the second electrical terminals of the plurality of first electrical devices to the second conductive trace that is on the second surface of the flexible substrate, said first and second conductive traces and said link means carrying an electrical current that energizes the plurality of first electrical devices; and
    (f) a biocompatible, flexible material encapsulating the flexible substrate, the first and second conductive traces, the link means, and the plurality of first electrical devices.

2. The flexible circuit of claim 1, further comprising a plurality of second electrical devices mounted in spaced-apart array along the second surface, each of said plurality of second electrical devices having:
    (a) a first electrical terminal; and
    (b) a second electrical terminal spaced apart from said first electrical terminal and in electrical contact with the second electrically conductive trace.

3. The flexible circuit of claim 2, wherein the link means electrically connect the second electrical terminals of the plurality of first electrical devices to the first electrical terminals on the plurality of second electrical devices, so that the electrical current carried by the first and second electrical traces and the link means flows through the plurality of first electrical devices, in series with the plurality of second electrical devices, and thus also energizes the plurality of second electrical devices.

4. The flexible circuit of claim 3, wherein the link means preferably comprise generally straight segments of wire.

5. The flexible circuit of claim 3, wherein the second terminals of the plurality of first electrical devices and the first terminals of the plurality of second electrical devices each face toward an edge of the flexible substrate, said link means comprising conductors that extend past said edge to connect the second terminals of the plurality of first electrical devices to the first terminals of the plurality of second electrical devices.

6. The flexible circuit of claim 2, wherein the link means comprise first conductors that extend between and are connected to the second electrical terminals of the plurality of first electrical devices and the second conductive trace, and second conductors that extend between and are connected to the first electrical terminals of the plurality of second electrical devices and the first conductive trace, so that the electrical current carried by the first and second electrical traces and the link means flows through the plurality of first electrical devices in parallel with the plurality of second electrical devices, and thus also energizes the plurality of second electrical devices.

7. The flexible circuit of claim 2, wherein the first and second conductive traces each comprise a conductive foil, the conductive foil of the first conductive trace having a plurality of first side arms extending transversely off an edge of the first surface of the flexible substrate, and the conductive foil of the second conductive trace having a plurality of second side arms extending transversely off an edge of the second surface, said link means comprising:
    (a) the plurality of first side arms, which are bent to connect to the first electrical terminals of the plurality of second electrical devices; and
    (b) the plurality of second side arms, which are bent to connect to the second electrical terminals of the plurality of first electrical devices.

8. The flexible circuit of claim 2, wherein the plurality of first and second electrical devices comprise light emitting devices for providing a light therapy at a treatment site within the patient's body.

9. The flexible circuit of claim 2, wherein the plurality of first and second electrical devices are mounted on the first and second surfaces of the flexible substrate using an adhesive.

10. The flexible circuit of claim 9, wherein the adhesive is electrically conductive and electrically couples the first electrical terminals of the plurality of first electrical devices to the first conductive trace, and the second electrical terminals of the plurality of second electrical devices to the second conductive trace.

11. The flexible circuit of claim 1, wherein the second conductive trace comprises a conductive foil having a plurality of side arms extending transversely off an edge of the second surface of the flexible substrate, said link means comprising the plurality of side arms, which are bent to connect to the second electrical terminals of the plurality of first electrical devices.

12. The flexible circuit of claim 11, wherein second surfaces of two flexible circuits are bonded together forming an assembly having first electrical devices mounted on opposite sides thereof.

13. A flexible circuit probe intended to be inserted into a patient's body and because of its flexibility and compact cross-sectional size, to be readily advanced to a treatment site in the patient's body, comprising:
    (a) a flexible, dielectric support having an elongate shape and generally extending along a longitudinal axis of the flexible circuit probe, said support having a first surface and a second surface;
    (b) treatment means, mounted on the first surface of the support, for providing a therapeutic treatment when energized with an electrical current;

(c) a first conductive circuit applied to the first surface of the support;

(d) a second conductive circuit applied to the second surface of the support, said first conductive circuit and said second conductive circuit being adapted to connect to a source of an electrical current;

(e) a plurality of conductive links that extend past an edge of the support, said conductive links electrically coupling the treatment means mounted on the first surface with the second conductive circuit; and (f) a biocompatible, flexible material that generally encapsulates the support, the treatment means, the first and second conductive circuits, and the plurality of conductive links.

14. The flexible circuit probe of claim 13, wherein the treatment means are also mounted on the second surface of the support, said plurality of conductive links electrically coupling the treatment means on the second surface with the first conductive circuit.

15. The flexible circuit probe of claim 14, wherein the treatment means include first and second electric terminals, said first electric terminals being electrically connected to the first conductive circuit for the treatment means mounted on the first surface, and said second electric terminals being electrically connected to the second conductive circuit, for the treatment means mounted on the second surface.

16. The flexible circuit probe of claim 15, wherein the plurality of conductive links are electrically connected to the second electric terminals of the treatment means mounted on the first surface of the support, and are electrically connected to the first electric terminals of the treatment means mounted on the second surface of the support.

17. The flexible circuit probe of claim 15, wherein a portion of the plurality of conductive links are electrically connected to the second electric terminals of the treatment means mounted on the first surface of the support, and to the second conductive circuit; and a remainder of the conductive links are electrically connected to the first electric terminals of the treatment means mounted on the second surface of the support, and to the first conductive circuit.

18. The flexible circuit probe of claim 14, wherein the treatment means are mounted to the first conductive circuit and to the second conductive circuit using a conductive adhesive.

19. The flexible circuit probe of claim 13, wherein the conductive links are generally U-shaped.

20. Tile flexible circuit probe of claim 13, wherein the conductive links are generally straight wire segments.

21. Tile flexible circuit probe of claim 13, wherein the conductive links comprise arms of the first and second conductive circuits that extend outwardly of the edge of the support and generally transverse to the longitudinal axis of the probe, said arms being deformed to couple to the treatment means.

22. The flexible circuit probe of claim 13, wherein the treatment means comprise a plurality of light emitting sources mounted on the support in spaced-apart array, for providing light therapy to the treatment site.

23. The flexible circuit probe of claim 22, wherein the material that encapsulates is substantially optically transparent.

24. The flexible circuit probe of claim 13, wherein one of an adhesive and a solder alloy are used to connect the conductive links to the treatment means.

25. The flexible circuit probe of claim 13, wherein the material that encapsulates defines an elongate flexible rod and protects the support and treatment means within the flexible rod.

26. The flexible circuit probe of claim 13, wherein the treatment means comprise a plurality of pairs of light emitting devices, one light emitting device of each pair being mounted on the first surface, and another light emitting device of each pair being mounted on the second surface of the support.

27. The flexible circuit probe of claim 26, wherein the light emitting devices comprising each pair are connected in parallel to the first and second conductive circuits.

28. The flexible circuit probe of claim 26, wherein the light emitting devices comprising each pair are connected in series with the first and second conductive circuits.

\* \* \* \* \*